United States Patent
Van Wolferen

(10) Patent No.: US 11,844,901 B2
(45) Date of Patent: Dec. 19, 2023

(54) SYSTEM AND METHOD FOR DETECTING AGITATION, DISCOMFORT AND/OR SELF-EXTUBATION DURING INTUBATION

(71) Applicant: KONINKLIJKE PHILIPS N.V., Eindhoven (NL)

(72) Inventor: Jeremy Van Wolferen, Murrieta, CA (US)

(73) Assignee: Koninklijke Philips N.V., Eindhoven (NL)

( * ) Notice: Subject to any disclaimer, the term of this patent is extended or adjusted under 35 U.S.C. 154(b) by 408 days.

(21) Appl. No.: 17/190,912

(22) Filed: Mar. 3, 2021

(65) Prior Publication Data
US 2021/0316098 A1    Oct. 14, 2021

Related U.S. Application Data

(60) Provisional application No. 63/006,797, filed on Apr. 8, 2020.

(51) Int. Cl.
*A61M 16/04* (2006.01)
*G05B 13/02* (2006.01)

(52) U.S. Cl.
CPC ....... *A61M 16/0493* (2014.02); *G05B 13/027* (2013.01); *A61M 2205/18* (2013.01); *A61M 2205/332* (2013.01)

(58) Field of Classification Search
CPC .............. A61M 16/04; A61M 16/0402; A61M 16/0488; A61M 16/0493
See application file for complete search history.

(56) References Cited

U.S. PATENT DOCUMENTS

| 5,862,801 A | 1/1999 | Wells |
| 3,256,427 A1 | 9/2012 | Chang |
| 2013/0281885 A1 | 10/2013 | Reynolds |
| 2014/0171817 A1 | 6/2014 | Blanch |
| 2014/0251328 A1 | 9/2014 | Doyle |

(Continued)

FOREIGN PATENT DOCUMENTS

| CN | 207837989 U | 9/2018 |
| JP | 2018201755 A | 12/2018 |

OTHER PUBLICATIONS

Gelinas eta al, The Critical-Care Pain Observation Tool (CPOT), 2006 (Year: 2006).*

(Continued)

*Primary Examiner* — Margaret M Luarca
(74) *Attorney, Agent, or Firm* — Daniel H. Brean; Andrew M. Gabriel

(57) ABSTRACT

A method of monitoring patient use of an endotracheal tube with a ventilator includes receiving in a controller, such as in a stand-alone monitoring device or in the ventilator itself, force data indicative of a biting force of the patient on the endotracheal tube, wherein the force data is based on force signals generated by a force sensor coupled to the endotracheal tube (e.g., either directly or by way of a bite block). The method further includes analyzing the force data in the controller, and determining in the controller from the analyzing of the force data that the force data is indicative of one or more of: (i) at least a predetermined threshold level of agitation or discomfort of the patient, and (ii) a current or likely attempt to self-extubate by the patient.

20 Claims, 5 Drawing Sheets

(56) References Cited

U.S. PATENT DOCUMENTS

2016/0206189 A1    7/2016   Aharon
2016/0228285 A1    8/2016   Delrio
2017/0028146 A1    2/2017   Nandigama

OTHER PUBLICATIONS

Sutari, M.M. et al., "Pain among mechanically ventilated patients in critical care units," J. Res. Med. Sci. Off. J. Isfahan Univ. Med. Sci., vol. 19, No. 8, pp. 726-732, Aug. 2014.
Lassence, D. de et al., "Impact of Unplanned Extubation and Reintubation after Weaning on Nosocomial Pneumonia Risk in the Intensive Care Unit A Prospective Multicenter Study," Anesthesiol. J. Am. Soc. Anesthesiol., vol. 97, No. 1, pp. 148-156, Jul. 2002.
Kiekkas, P. et al., "Unplanned extubation in critically ill adults: clinical review," Nurs. Crit. Care, vol. 18, No. 3, pp. 123-134, 2012.
Moons, P. et al., "Self-extubation risk assessment tool: predictive validity in a real-life setting," Nurs. Crit. Care, vol. 13, No. 6, pp. 310-314, 2008.
Selvan, K. et al., "Self-extubation in ICU patients," Southwest Respir. Crit. Care Chron., vol. 2, No. 8, pp. 31-34, 2014.
Moons, "Development of a risk assessment tool for deliberate self-extubation in intensive care patients," Intensive Care Med., Abstract, Jul. 2004.
Shibusawa, M. et al., "Functional near-infrared spectroscopy study on primary motor and sensor cortex response to clenching", Neuroscience Letters, Elsevier, Amsterdam, NL, vol. 449, No. 2, (Jan. 9, 2009), pp. 98-102, XP025742552.
International Search Report for PCT/EP2021/058828 filed Apr. 6, 2021.

* cited by examiner

SYSTEM AND METHOD FOR DETECTING AGITATION, DISCOMFORT AND/OR SELF-EXTUBATION DURING INTUBATION

CROSS-REFERENCE TO RELATED APPLICATIONS

This patent application claims the priority benefit under 35 U.S.C. § 119(e) of U.S. Provisional Application No. 63/006,797 filed on Apr. 8, 2020, the contents of which are herein incorporated by reference.

BACKGROUND OF THE INVENTION

1. Field of the Invention

The disclosed concept pertains to systems and methods for providing mechanical ventilation to patients, and, in particular, to a system and method for detecting patient agitation, discomfort and/or self-extubation attempts while being intubated with an endotracheal tube.

2. Description of the Related Art

Mechanical ventilation (MV) is a life-saving therapy. It is typically instituted when a patient is unable to maintain adequate ventilation or oxygenation, and hence gas exchange, on their own. One of the most widely used MV techniques in intensive care units (ICU) is invasive ventilation which provides access to the lower airways through an artificial airway called an endotracheal tube (ET tube). Hence, it establishes a major advance in the management of patients with respiratory distress. Despite the undoubted benefits of MV, there exists a significant number of patients who experience agitation, discomfort, or pain over the course of the therapy, whether being at rest or during routine clinical procedures and interventions.

Discomfort can be associated with multiple factors. Ventilation management itself is a major determinant. It is well known that the ventilator apparatus (i.e., endotracheal tube for invasive ventilation) as well as erroneous ventilator settings or inappropriate modes of ventilation may have a significant impact on the patient's comfort and well-being. Clinical interventions also play a significant role. For example, patient repositioning, oral care, tracheal suctioning and blood line insertion/removal, although being part of the routine practice, are very likely to induce discomfort and agitation.

Assessment of agitation, discomfort, or pain during intubation and mechanical ventilation is particularly difficult in critical patients because they are mostly unable to self-report due to the underlying clinical condition, the interference with speech caused by the ET tube, or the institution of sedative drugs. However, if agitation is not detected and not eased promptly and efficiently, patient recovery may be adversely affected. This can lead to worse patient outcomes, extended length of stay, and increased hospitalization costs.

In addition, discomfort may make a patient prone to self-extubation. Being intubated is uncomfortable for patients, particularly for those awake, alert and spontaneously breathing, and can occasionally lead them to try to pull out the endotracheal tube. One study reports that the estimated incidence of unplanned extubation (whether accidental, due to the personnel's inappropriate manipulation of the ET tube, or deliberate, due to the patient's action) is around 10%, with 60% of these unplanned extubations requiring re-intubation. The clear majority (62.8%-96.4%) of unplanned extubations in adult ICUs are the result of patient self-extubation. This is typically attributed to patient agitation. While not directly linked with increased mortality, unplanned extubation has been associated with longer times on mechanical ventilation and longer ICU and hospital stay, while re-intubation is recognized as a risk factor for nosocomial pneumonia.

One prior art tool that has been developed for assessing the risk of self-extubation is known as the SERAT score. The SERAT score is derived by a classification scheme that is based on the Glasgow Coma Scale and the Bloomsbury Sedation Score. The SERAT score, however, is merely a risk assessment tool, and is not aimed at providing continuous monitoring since the evaluation of the SERAT scores is performed at certain times every day, like, for instance, at the start of each nursing shift. In addition, both Glasgow Coma Scale and Bloomsbury Sedation Score have drawn criticism because of their poor inter-rater reliability and lack of prognostic utility. Nevertheless, it has been demonstrated that the SERAT can correctly identify the patients at risk for self-extubation, but with a high number of false-positive identifications. If clinically deployed, this will result in a high number of false alarms, which is undesirable in an ICU setting.

SUMMARY OF THE INVENTION

Accordingly, it is an object of the present invention to provide, in one embodiment, a method of monitoring patient use of an endotracheal tube with a ventilator that includes receiving in a controller, such as in a stand-alone monitoring device or in the ventilator itself, force data indicative of a biting force of the patient on the endotracheal tube, wherein the force data is based on force signals generated by a force sensor coupled to the endotracheal tube (e.g., either directly or by way of a bite block). The method further includes analyzing the force data in the controller, and determining in the controller from the analyzing of the force data that the force data is indicative of one or more of: (i) at least a predetermined threshold level of agitation or discomfort of the patient, and (ii) a current or likely attempt to self-extubate by the patient.

In another embodiment, a system for monitoring use of an endotracheal tube with a ventilator by a patient is provided that includes a force sensor coupled to the endotracheal tube, the force sensor being structured and configured to generate force signals in response to a biting force of the patient, and a controller, which may be part of a stand-alone monitoring device or the ventilator itself. The controller is structured and configured for receiving force data indicative of the biting force of the patient based on the force signals, analyzing the force data in the controller, and determining from the analyzing of the force data that the force data is indicative of one or more of: (i) at least a predetermined threshold level of agitation or discomfort of the patient, and (ii) a current or likely attempt to self-extubate by patient.

In still another embodiment, a bite block for an endotracheal tube is provided that includes a main body and a force sensor coupled to the main body. The force sensor is structured and configured to generate force signals in response to a biting force of the patient.

In yet another embodiment, an apparatus for monitoring the use of an endotracheal tube is provided. The apparatus includes a controller structured and configured for receiving force data indicative of the biting force of the patient based on force signals generated by a force sensor coupled to the endotracheal tube, the force sensor being structured and configured to generate the force signals in response to a biting force of the patient, analyzing the force data in the controller, and determining from the analyzing of the force data that the force data is indicative of one or more of: (i) at least a predetermined threshold level of agitation or discomfort of the patient, and (ii) a current or likely attempt to self-extubate by the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
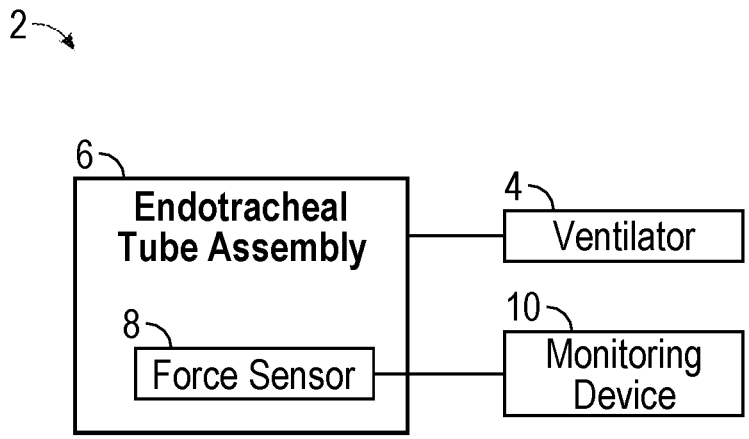
FIG. 1 is a schematic diagram of a system for detecting and monitoring patient agitation and discomfort and/or self extubation attempts according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "number" shall mean one or an integer greater than one (i.e., a plurality).

As used herein, the term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept, as described in greater detail herein in connection with various particular exemplary embodiments, provides an enhanced endotracheal tube system that can provide continuous surveillance of intubated patients for signs of agitation or discomfort. In one non-limiting exemplary embodiment, the endotracheal tube system employs an enhanced bite block for monitoring purposes. A bite block is an add-on that is placed around endotracheal tube at the level of the patient's mouth (typically between markings of 18 and 26 cm in an adult-sized ET tube; pediatric cm markings are less; actual bite block location on the tube may vary). The primary purpose of a bite block is to prevent patients from damaging or occluding the endotracheal tube with their teeth (e.g., by closing their mouth) and to protect against rupturing the pilot balloon of the endotracheal tube. The disclosed concept is based on the fact that agitation and/or discomfort are often expressed by teeth grinding (for example, people with problems of anxiety are prescribed with night guards). In particular, the disclosed concept, in one exemplary embodiment described herein, provides for the combination and integration of a bite force sensor with a bite block, or alternatively, in another exemplary embodiment described herein, directly with an endotracheal tube. The bite force sensor encircles the bite block, or endotracheal tube, where the teeth typically meet the endotracheal tube. Such a system is minimally obtrusive to the patient and does not interfere with the interventions/actions of the medical team.

As described elsewhere herein, the system, as implemented in the various exemplary embodiments, monitors the patient and alerts the care team to intervene when increased signs of agitation are detected based on the measurements made by the bite force sensor. Also, the system of the disclosed concept will reduce the incidence of self-extubation because patients typically bite down on the endotracheal tube when agitated and prior to pulling the tube out. The harder the patient is biting down on the endotracheal tube or bite block, as the case may be, the more agitated the patient is and the more likely they are to self-extubate.

Humans can relatively easily identify emotions, like discomfort or pain, based on facial expressions. Such cues, however, are frequently subtle and short in duration and can be overlooked, particularly in a critical care environment. Moreover, data overload adds extra burden to the already overtaxed medical personnel and eventually results in them paying less attention to physical expressions and behavior of the patient. Therefore, having a solution, like the one provided by the disclosed concept, to monitor agitation and discomfort of patients who are intubated and mechanically ventilated is a clear unmet need.

Furthermore, as noted above, unplanned extubation is another problem that can be overcome by the disclosed concept. Prevention of unplanned extubation needs to be examined from two distinct aspects based on the type of extubation. Accidental extubation can mostly be mitigated if medical personnel are trained on the use of guidelines for proper manipulation and maintenance of the endotracheal tube during clinical practice. On the other hand, prevention of self-extubation requires regular surveillance or monitoring of the patient by the medical team. In particular, nursing care is an important factor that contributes to the patient's likelihood to self-extubate. It has been shown that absence of the attending nurse or respiratory therapist or other caregiver from the bedside is the most important predictor for self-extubation. Continuous bedside presence, or even remote surveillance, of the patient by a member of the health care team, however, is a major challenge for clinical institutions. Staff overload and high bed occupancy have led to reduced surveillance or monitoring and hence increased risks of self-extubation. Thus, providing a solution such as the disclosed concept that can ensure 24/7 monitoring of intubated patients and can alert the care team of predicted and detected self-extubation would increase their vigilance and help them undertake specific risk-reducing interventions upon identification of a predicted or actual self-extubation attempt.

FIG. 1 is a schematic diagram of a system 2 for detecting and monitoring patient agitation and discomfort and/or self extubation attempts according to an exemplary embodiment of the disclosed concept. As seen in FIG. 1, system 2 includes a ventilator 4 that is structured to move breathable air into and out of the lungs of a patient. An endotracheal tube assembly 6 is operatively coupled to ventilator 4 for delivering the breathable gas to the lungs of the patient. Endotracheal tube assembly 6 includes a force sensor 8 that is structured and configured to measure a bite force being applied by the patient at any given time. Force sensor 8 may be any suitable sensing device, such as a sensor array, that includes a number of sensing elements that are capable of measuring the force that is applied to an endotracheal tube by the teeth of a patient. For example, and without limitation, force sensor 8 may be the FlexiForce® ESS301 load/force sensor that is commercially available from Tekscan, Inc. of South Boston Massachusetts. In the exemplary embodiment, force sensor 8 is able to handle increased levels of humidity in order to be well-suited to the humid and wet conditions at a patient's mouth due to, for example, the presence of secretions and saliva. Also, in the exemplary embodiment, force sensor 8 needs to be sufficiently wide because endotracheal tube assembly 6 slides in and out with patient movement. Thus, in embodiments where it is integrated with a bite block, it will cover, for example and without limitation, 40% or more (or 50%, 60% or 70% or more) of the outer surface area of the bite block. In others particular embodiments (with or without a bite block), force sensor 8 is, for example and without limitation, 6-8 cm wide with the cm markings being printed on force sensor 8 (either by the ET tube manufacturer or by a third-party) so that the medical team can place the ET tube at the proper location within the patient's trachea.

As seen FIG. 1, system 2 also includes a monitoring device 10 that, in the illustrated exemplary embodiment, is structured to be placed bedside with the patient. In this exemplary embodiment, monitoring device 10 is a small standalone monitor structured and configured to analyze and display information to the clinician and alert them with alarms such as low, medium, or high priority or green zone, yellow zone, or red zone alerts, etc., as the patient becomes more agitated/bites down harder. Force sensor 8 is electrically connected to monitoring device 10 so that the force measurements made by force sensor 8 can be provided to monitoring device 10 for analysis thereby as described herein (i.e., in this embodiment, monitoring device 10 includes the "brains" of system 2). The electrical connection between force sensor 8 and monitoring device 10 may be wired or wireless. For example, the electrical connection may be made by way of a ribbon cable assembly or other suitable wire assembly in the case of a wired connection, and may be made by way of a Bluetooth® or other suitable wireless protocol network in the case of a wireless connection.

Figure 2:
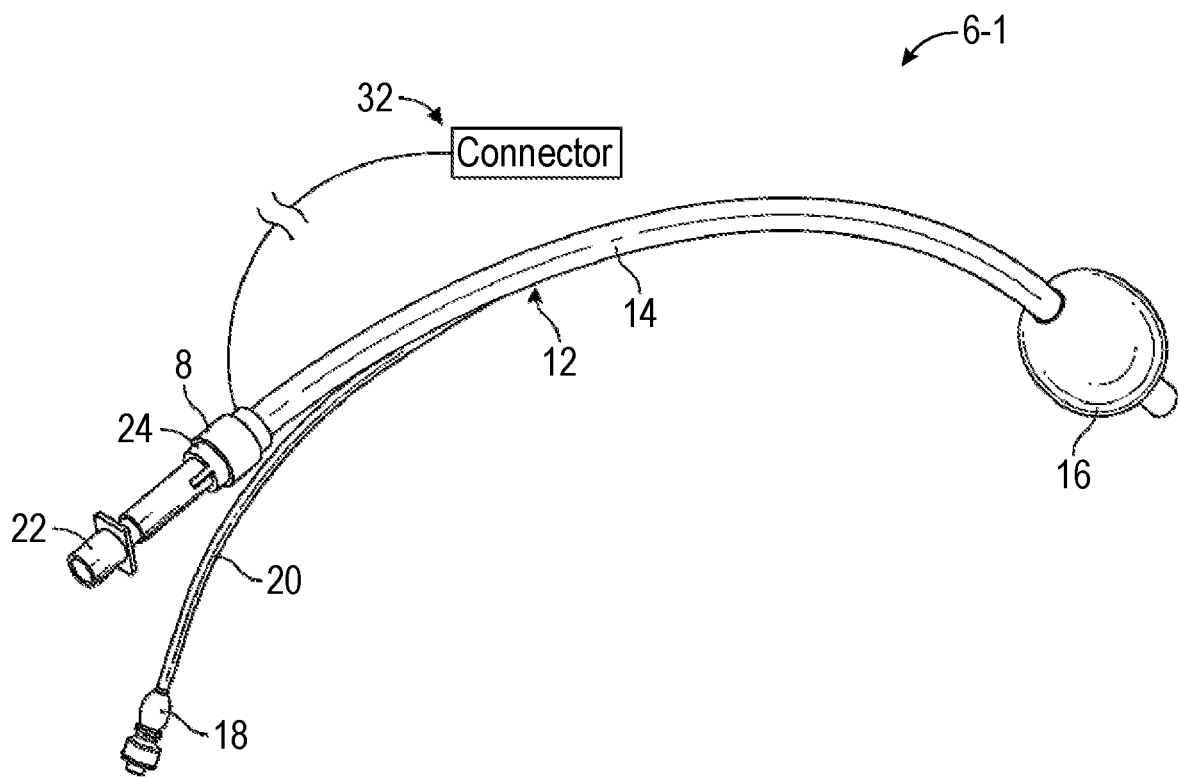
FIG. 2 is a schematic diagram of an endotracheal tube assembly forming part of the system of FIG. 1 according to one particular, exemplary embodiment of the disclosed concept.

FIG. 2 is a schematic diagram of endotracheal tube assembly 6, labelled 6-1 for clarity, according to one particular, exemplary embodiment of the disclosed concept. As described in more detail below, the embodiment of FIG. 2 is one where the force sensor is integrated as part of a bite block.

Referring to FIG. 2, endotracheal tube assembly 6-1 includes an endotracheal tube 12. Endotracheal tube 12 includes a main breathing tube having an inflatable cuff 16 provided at a first end thereof that is inserted into the trachea of the patient. Inflatable cuff 16 is inflated after insertion of main breathing tube 14 into the patient's trachea by way of a pilot balloon 18 (having a one-way valve) and a cuff inflation line 20 in order to hold endotracheal tube 12 in place. A connector 22 is provided at a second end of main breathing tube 14. Connector 22 is structured to stick out of the mouth of the patient and be connected to ventilator 4 by a suitable delivery tube.

Figure 3:
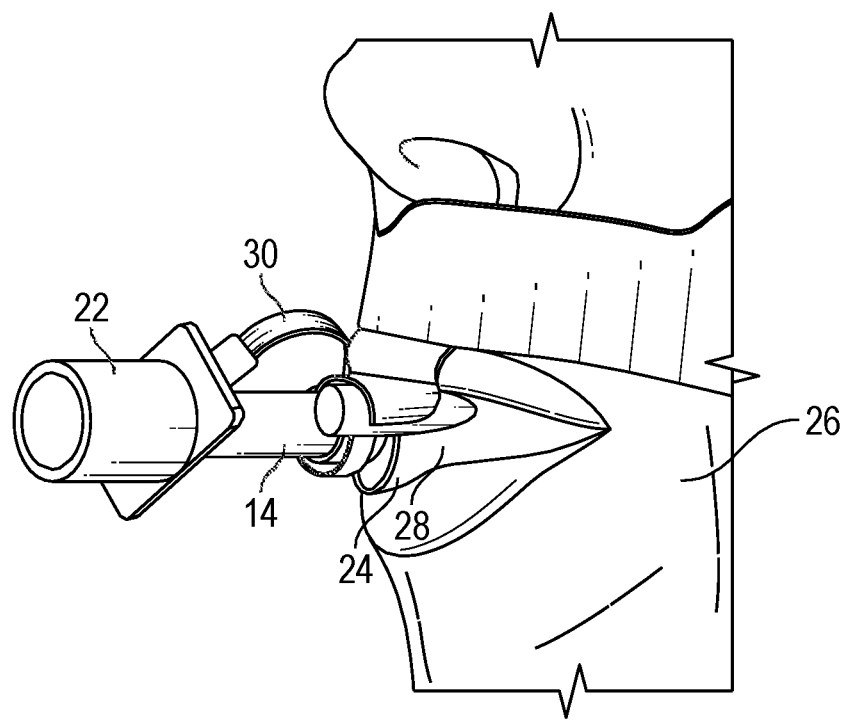
FIG. 3 is a view showing the endotracheal tube assembly of FIG. 2 extending from the mouth of a patient.
Figure 4:
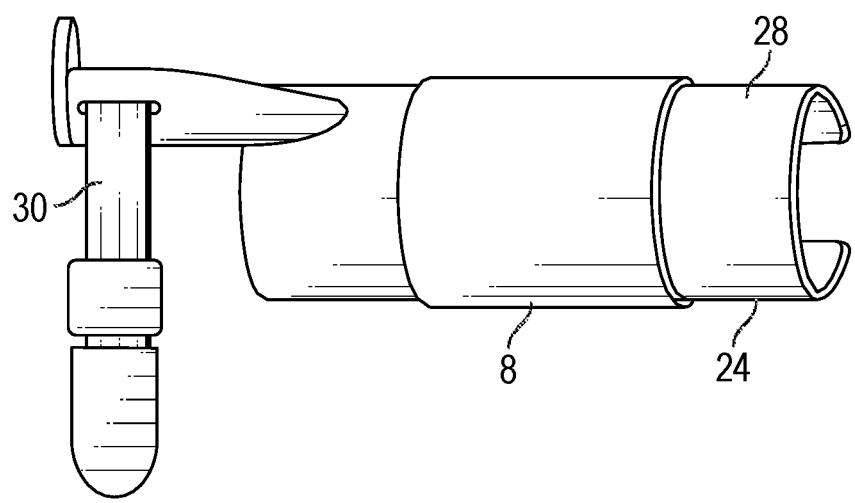
FIGS. 4 and 5 are side and isometric views, respectively, of a bite block forming part of the endotracheal tube assembly of FIG. 2.
Figure 5:
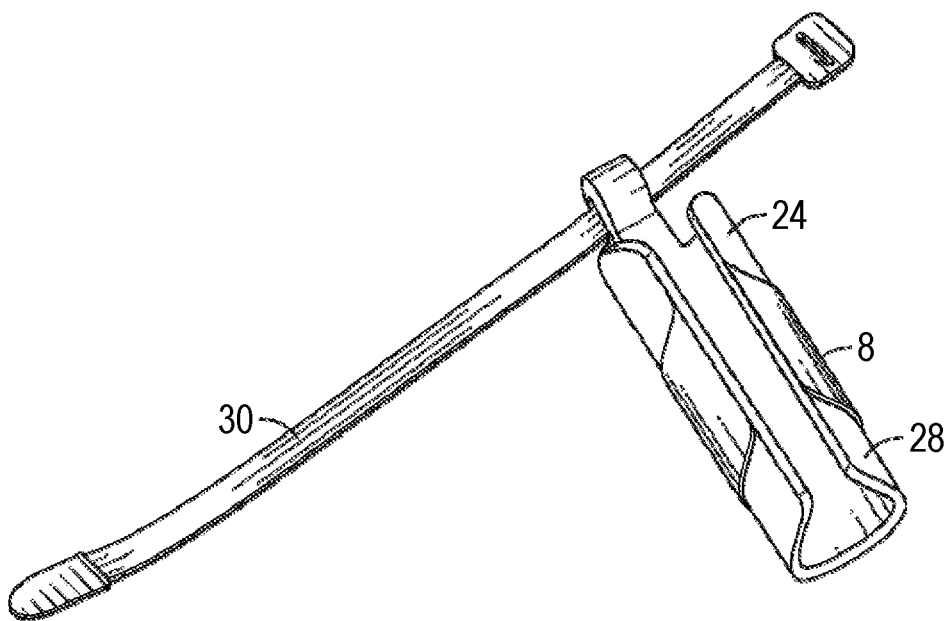

In addition, endotracheal tube assembly 6-1 also includes a bite block 24 that is provided at the second end of endotracheal tube 12. A close up of bite block 24 and connector 22 extending from the mouth of a patient 26 is shown in FIG. 3. FIGS. 4 and 5 are schematic diagrams of bite block 24 according to the exemplary embodiment of the disclosed concept. As seen in FIGS. 2-5, bite block 24 has a main body 28 that wraps around the second end of main breathing tube 14. Force sensor 8 is attached to the external surface of main body 28. A securing strap 30 for securing bite block 24 to main breathing tube 14 is provided at an end of main body 28. In addition, as seen FIG. 2, endotracheal tube assembly 12 also further includes a connector assembly 32, such as a ribbon connector assembly, for connecting force sensor 8 to monitoring device 10.

Figure 6:
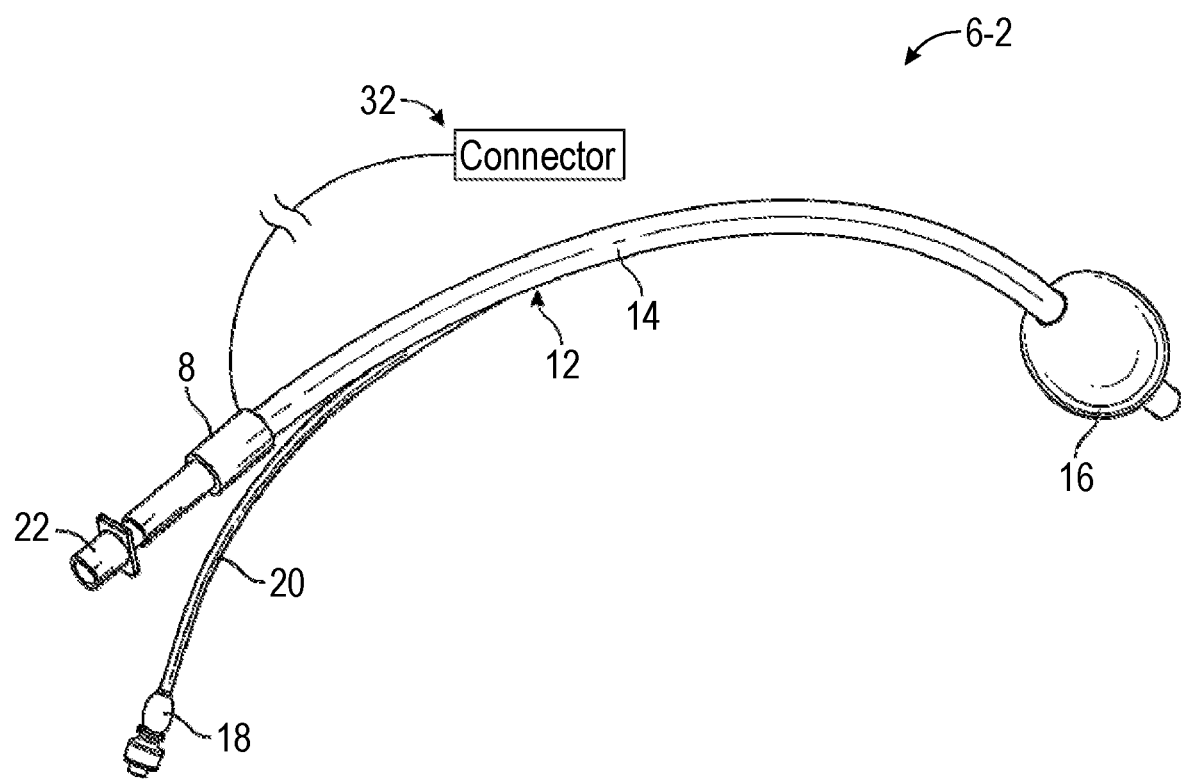
FIG. 6 is a schematic diagram of an endotracheal tube assembly forming part of the system of FIG. 1 according to another, alternative particular, exemplary embodiment of the disclosed concept.

FIG. 6 is a schematic diagram of endotracheal tube assembly 6, labelled 6-2 for clarity, according to an alternative particular, exemplary embodiment of the disclosed concept. Endotracheal tube assembly 6-2 is similar to endotracheal tube assembly 6-1, and like parts are labelled with like reference numerals. However, as seen in FIG. 6, this embodiment does not employ a bite block, and instead force sensor 8 is connected directly to the outer surface of main breathing tune 14.

Figure 7:
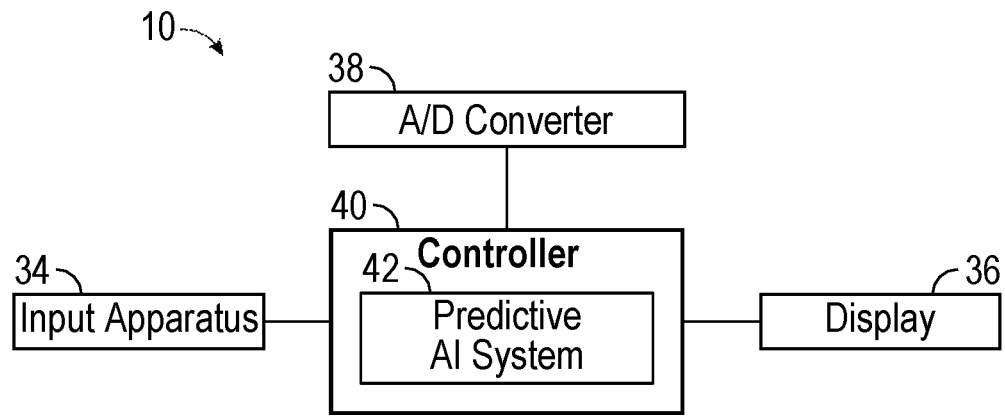
FIG. 7 is a schematic diagram of a monitoring device forming part of the system of FIG. 1 according to an exemplary embodiment of the disclosed concept.

FIG. 7 is a schematic diagram of monitoring device 10 according to an exemplary embodiment of the disclosed concept. Monitoring device 10 includes an input apparatus 34 (e.g., a plurality of buttons), a display 36, an A/D converter 38 and a controller 40. A user is able to provide input controller 40 using input apparatus 34, and controller 40 provides output signals to display 36 to enable display 36 to display information to the user (e.g., a clinician) as described in detail herein. A/D converter 38 is structured to receive analog signals from force sensor 8 and convert them to digital form for use by controller 40. The memory portion of controller 40 has stored therein a number of routines that are executable by the processor portion of controller 40. One or more of the routines implement (by way of computer/processor executable instructions) a software application that is configured (by way of one or more algorithms) to, among other things, received the force measurements that are generated by force sensor 8 and analyze them in order to determine the degree of agitation or discomfort of the patient (e.g., that at least a predetermined threshold level of agitation or discomfort is being experienced by the patient) and/or identify possible attempts by the patient to self extubate. In the non-limiting exemplary embodiment, as seen in FIG. 7, controller 40 is provided with a predictive Artificial Intelligence AI system 42, such as a trained neural network or other supervised learning systems, for this purpose. In such an embodiment, training of predictive AI system 42 can be done by collecting raw data of intubated patients and manually categorizing them into two classes: comfort and agitation/discomfort. Once trained, predictive AI system 42 will output a probability or likelihood of the patient being in agitation; this can be used as an indicator for monitoring or alerting systems implemented in monitoring device 10. To equip monitoring device 10 with this capability, specialized processing chips may need to be embedded as part of controller 40, to which the output signals of force sensor 8 (i.e., amount of force in time) will be fed. In the exemplary embodiment, force sensor 8 is designed to be sensitive with precise units of measure in PSI (such as a scale from 1-500).

Figure 8:
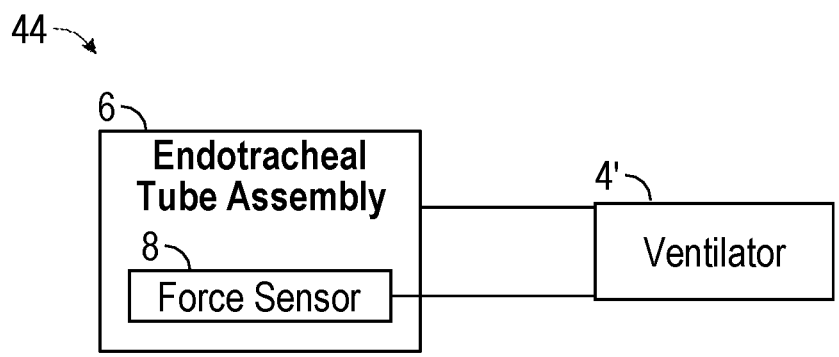
FIG. 8 is a schematic diagram of a system for detecting and monitoring patient agitation and discomfort and/or self extubation attempts according to an alternative exemplary embodiment of the disclosed concept.
Figure 9:
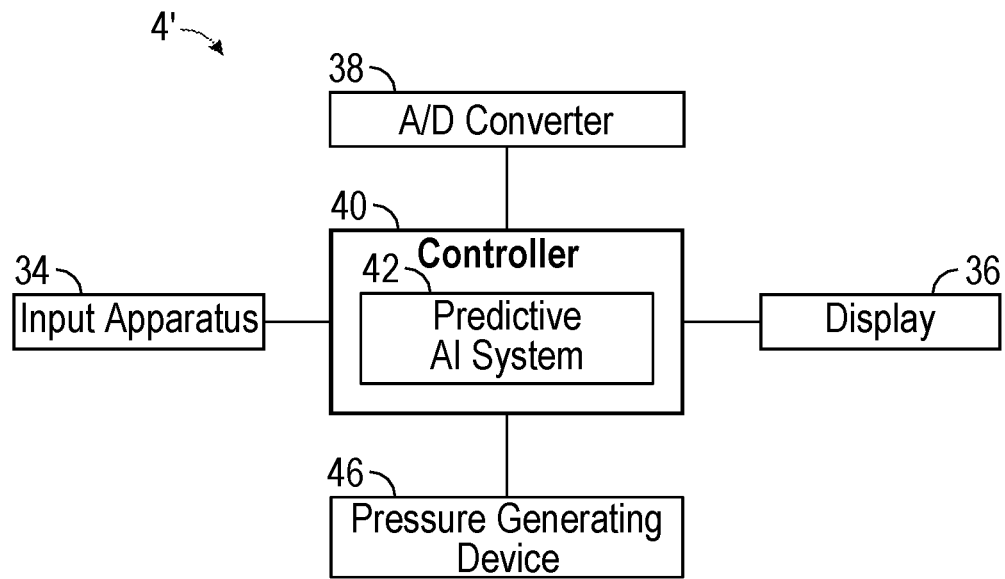
FIG. 9 is a schematic diagram of a ventilator according to an exemplary embodiment of the disclosed concept.

FIG. 8 is a schematic diagram of a system 44 for detecting and monitoring patient agitation and discomfort and/or self extubation attempts according to an alternative exemplary embodiment of the disclosed concept. System 44 is similar to system 2, and like parts are labeled with like reference numerals. System 44 differs in that it includes an alternative ventilator 4' and does not include stand-alone monitoring device 10. FIG. 9 is a schematic diagram of ventilator 4' according to an exemplary embodiment of be disclosed concept. As seen in FIG. 9, ventilator 4' includes a pressure generating device 46 for generating the flow of breathable gas for the patient. Ventilator 4' also includes many of the parts included as part of monitoring device 10, with like parts being labeled with like reference numerals. Thus, ventilator 4' is able to receive and analyze the force measurements made by force sensor 8 as described elsewhere here in in order to provide feedback and alarms regarding patient agitation and discomfort and/or patient self extubation attempts as described elsewhere herein.

Figure 10:
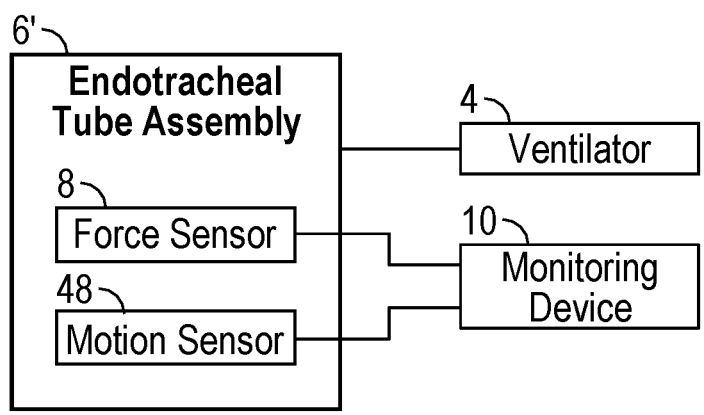
FIGS. 10 and 11 are schematic diagrams of systems for detecting and monitoring patient agitation and discomfort and/or self extubation attempts according to further exemplary embodiments of the disclosed concept.

FIG. 10 is a schematic diagram of a system 2' for detecting and monitoring patient agitation and discomfort and/or self extubation attempts according to another alternative exemplary embodiment of the disclosed concept. System 2' is similar to system 2, and like parts are labeled with like reference numerals. System 2' differs in that it includes an alternative endotracheal tube 6' that, as seen in FIG. 10, further includes a motion sensor 48 structured and configured to detect movement of endotracheal tube assembly 6'. In this embodiment, motion sensor 48 may be integrated as part of bite block 24 (FIG. 2), or may be attached directly to main breathing tube 14 (FIG. 6). Motion sensor 48 maybe any type of suitable motion-sensing device, such as, without limitation, an accelerometer. For example, motion sensor 48 could be the MEMS digital output motion sensor: ultra-low-power high-performance 3-axis accelerometer commercially available from STMicroelecroncis. In this embodiment, detection of agitation and discomfort and/or attempts by the patient to self-extubate by pulling the endotracheal tube out can be assessed by analyzing the force applied by the patient as described elsewhere herein (e.g., to determine that at least a predetermined threshold level of agitation or discomfort is being experienced by the patient). In addition, monitoring of agitation and discomfort and/or self-extubation attempts can also be augmented with motion analysis from the embedded motion sensor 48. In such an embodiment, predictive AI system 42 (FIG. 7) of monitoring device 10 will be further trained with motion data from a device similar to motion sensor 48. This embodiment could predict likelihood of impending self-extubation and also may help indicate if a self-extubation is likely happening in "real time". The latter would be valuable to alert the clinician, as many times there is a delay in notification to the ICU nurse or respiratory therapist when a patient self-extubates.

Figure 11:
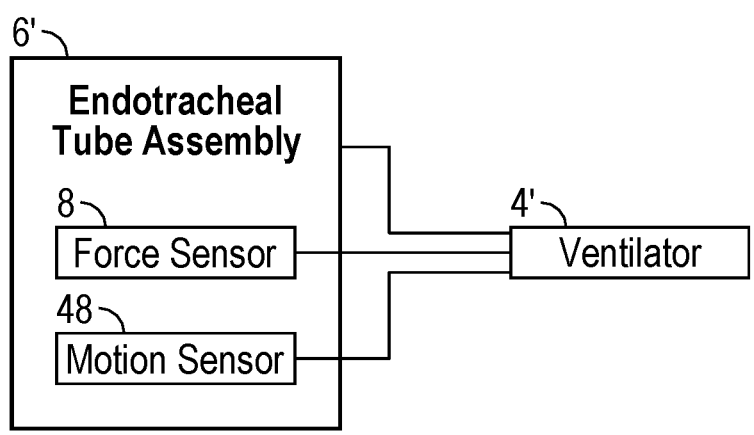

FIG. 11 is a schematic diagram of a system 44' for detecting and monitoring patient agitation and discomfort and/or self extubation attempts according to still another alternative exemplary embodiment of the disclosed concept. System 44' is similar to system 44, and like parts are labeled with like reference numerals. System 44' differs in that it includes alternative endotracheal tube 6' as just described so that monitoring of agitation and discomfort and/or self-extubation attempts can also be augmented with motion analysis from the embedded motion sensor 48. In such an embodiment, predictive AI system 42 (FIG. 9) of ventilator 4' will be further trained with motion data from a device similar to motion sensor 48. This embodiment could predict likelihood of impending self-extubation and also may help indicate if a self-extubation is likely happening in "real time".

Moreover, the disclosed concept can also be helpful for adjusting patient sedation levels. If the patient is agitated and biting down on their tube, they may need more sedation. The disclosed concept may thus be used to help detect agitation earlier than how it is currently done. So, in short, the disclosed concept does not just have extubation related benefits. Rather, it is also helpful for the medical team in assessing the patient's level of sedation (medically induced coma) for sedation titration of a common medication used for sedation, such as Propofol.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring use of an endotracheal tube with a ventilator by a patient, comprising:
receiving, in a controller, force data indicative of a biting force of the patient on the endotracheal tube, the force data being based on force signals generated by a force sensor coupled to the endotracheal tube at a portion of the endotracheal tube that is configured to be positioned inside the patient's mouth;
analyzing the force data in the controller; and
determining in the controller from the analyzing of the force data that the force data is indicative of one or more of: (i) at least a predetermined threshold level of agitation or discomfort of the patient, and (ii) a current or likely attempt to self-extubate by the patient.

2. The method according to claim 1, further comprising generating a message and/or an alarm in response to the determining.

3. The method according to claim 1, wherein the controller is structured and configured to implement a predictive Artificial Intelligence (AI) system, and wherein the analyzing and determining is performed by the predictive AI system.

4. The method according to claim 3, wherein the predicative AI system is a trained artificial neural network.

5. The method according to claim 1, wherein the endotracheal tube is part of an endotracheal tube assembly, wherein the endotracheal tube assembly includes a bite block that is attached to a main breathing tube, and wherein the force sensor is directly attached to an exterior surface of the bite block.

6. The method according to claim 1, wherein the endotracheal tube is part of an endotracheal tube assembly including a main breathing tube, and wherein the force sensor is directly attached to an exterior surface of the main breathing tube.

7. The method according to claim 1, further comprising:
receiving in the controller motion data indicative of movement of the endotracheal tube by the patient, the motion data being based on motion signals generated by a motion sensor coupled to the endotracheal tube; and
analyzing the motion data in the controller;
wherein the determining comprises determining in the controller from the analyzing of the force data and the analyzing of the motion data that at least one of the force data and the motion data is indicative of one or more of: (i) at least a predetermined threshold level of agitation or discomfort of the patient, and (ii) a current or likely attempt to self-extubate by the patient.

8. The method according to claim 7, wherein the endotracheal tube is part of an endotracheal tube assembly, wherein the endotracheal tube assembly includes a bite block that is attached to a main breathing tube, and wherein the force sensor and the motion sensor are directly attached to an exterior surface of the bite block.

9. A computer program product, comprising a non-transitory computer usable medium having a computer readable program code embodied therein, the computer readable program code being adapted and configured to be executed to implement a method of monitoring use of the endotracheal tube as recited in claim 1.

10. The method according to claim 1, further comprising, responsive to determining that the force data is indicative of at least a predetermined threshold level of agitation or discomfort of the patient, titrating a medication being used for sedation of the patient.

11. A system for monitoring use of an endotracheal tube with a ventilator by a patient, comprising:
a force sensor coupled to the endotracheal tube at a portion of the endotracheal tube that is configured to be positioned inside the patient's mouth, the force sensor being structured and configured to generate force signals in response to a biting force of the patient;
a controller structured and configured for:
receiving force data indicative of the biting force of the patient based on the force signals;
analyzing the force data in the controller; and
determining from the analyzing of the force data that the force data is indicative of one or more of: (i) at least a predetermined threshold level of agitation or discomfort of the patient, and (ii) a current or likely attempt to self-extubate by the patient.

12. The system according to claim 11, wherein the controller is further structured and configured for generating a message and/or an alarm in response to the determining.

13. The system according to claim 11, further comprising a bite block that is attached to a main breathing tube of the endotracheal tube, wherein the force sensor is directly attached to an exterior surface of the bite block.

14. The system according to claim 11, wherein the force sensor is directly attached to an exterior surface of a main breathing tube of the endotracheal tube.

15. The system according to claim 11, further comprising a motion sensor coupled to the endotracheal tube, wherein the controller is structured and configured for:
receiving motion data indicative of movement of the endotracheal tube by the patient, the motion data being based on motion signals generated by the motion sensor; and
analyzing the motion data in the controller;
wherein the determining comprises determining in the controller from the analyzing of the force data and the analyzing of the motion data that at least one of the force data and the motion data is indicative of one or more of: (i) at least a predetermined threshold level of agitation or discomfort of the patient, and (ii) a current or likely attempt to self-extubate by the patient.

16. The system according to claim 15, wherein the endotracheal tube is part of an endotracheal tube assembly, wherein the endotracheal tube assembly includes a bite block that is attached to a main breathing tube, and wherein the force sensor and the motion sensor are directly attached to an exterior surface of the bite block.

17. An apparatus for monitoring use of an endotracheal tube by a patient, comprising:
a controller structured and configured for:
receiving force data indicative of the biting force of the patient based on force signals generated by a force sensor coupled to the endotracheal tube at a portion of the endotracheal tube that is configured to be positioned inside the patient's mouth, the force sensor being structured and configured to generate the force signals in response to a biting force of the patient;
analyzing the force data in the controller; and
determining from the analyzing of the force data that the force data is indicative of one or more of: (i) at least a predetermined threshold level of agitation or discomfort of the patient, and (ii) a current or likely attempt to self-extubate by the patient.

18. The apparatus according to claim 17, wherein the controller is structured and configured for:
receiving motion data indicative of movement of the endotracheal tube by the patient, the motion data being based on motion signals generated by the motion sensor; and
analyzing the motion data in the controller;
wherein the determining comprises determining in the controller from the analyzing of the force data and the analyzing of the motion data that at least one of the force data and the motion data is indicative of one or more of: (i) at least a predetermined threshold level of agitation or discomfort of the patient, and (ii) a current or likely attempt to self-extubate by the patient.

19. The apparatus according to claim 17, wherein the controller is further structured and configured for generating a message and/or an alarm in response to the determining.

20. The apparatus according to claim 17, wherein the controller is structured and configured to implement a predictive AI system, and wherein the analyzing and determining is performed by the predictive AI system.

* * * * *